US012697168B2

(12) United States Patent
Howard et al.

(10) Patent No.: US 12,697,168 B2
(45) Date of Patent: Aug. 4, 2026

(54) PULSED FIELD ABLATION CATHETERS WITH ENHANCED FIELD SMART ELECTRODES

(71) Applicant: Medtronic, Inc., Minneapolis, MN (US)

(72) Inventors: Brian T. Howard, Minneapolis, MN (US); Timothy G. Laske, Shoreview, MN (US); Kenneth C. Gardeski, Inverness, FL (US); Gonzalo Martinez, Mendota Heights, MN (US); Mark T. Stewart, Lino Lakes, MN (US); Lars M. Mattison, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 1049 days.

(21) Appl. No.: 17/697,523

(22) Filed: Mar. 17, 2022

(65) Prior Publication Data

US 2022/0296295 A1      Sep. 22, 2022

Related U.S. Application Data

(60) Provisional application No. 63/162,596, filed on Mar. 18, 2021.

(51) Int. Cl.
*A61B 18/14* (2006.01)
*A61B 18/16* (2006.01)
*A61B 18/00* (2006.01)

(52) U.S. Cl.
CPC .......... *A61B 18/1492* (2013.01); *A61B 18/16* (2013.01); *A61B 2018/00083* (2013.01); *A61B 2018/00136* (2013.01); *A61B 2018/0022* (2013.01); *A61B 2018/00577* (2013.01); *A61B 2018/162* (2013.01)

(58) Field of Classification Search
CPC ................ A61B 18/1492; A61B 18/16; A61B 2018/00083; A61B 2018/00119; A61B 2018/00136; A61B 2018/0022; A61B 2018/00577; A61B 2018/1467; A61B 2018/162
See application file for complete search history.

(56) References Cited

U.S. PATENT DOCUMENTS 5,662,108 A      9/1997  Budd et al.
6,939,309 B1    9/2005  Beatty et al.
(Continued)

OTHER PUBLICATIONS

International Search Report and Written Opinion for Application No. PCT/US2022/020860 dated Jun. 22, 2022 (8 pages).
(Continued)

*Primary Examiner* — Khadijeh A Vahdat
(74) *Attorney, Agent, or Firm* — Michael Best & Friedrich LLP

(57) ABSTRACT

A medical device including an elongate body having a proximal portion and a distal portion. A plurality of active electrodes is coupled to the distal portion of the elongate body and being configured to electrically couple to a source of pulsed electric field energy. At least one passive electrode is coupled to the elongate body and is not configured to electrically couple to the source of pulsed electric field energy, the at least one passive electrode being configured to passively extend or focus an electric field generated by the plurality of active electrodes.

13 Claims, 5 Drawing Sheets

(56)        References Cited

U.S. PATENT DOCUMENTS

| | | | |
|---|---|---|---|
| 2014/0052120 A1* | 2/2014 | Benscoter .......... | A61B 18/1492 |
| | | | 606/41 |
| 2014/0276755 A1* | 9/2014 | Cao ......................... | A61N 5/00 |
| | | | 607/101 |
| 2014/0330262 A1* | 11/2014 | Jannicke ................ | A61B 18/02 |
| | | | 606/21 |
| 2015/0305800 A1 | 10/2015 | Trieu | |
| 2015/0374436 A1* | 12/2015 | Subramaniam .... | A61B 18/1492 |
| | | | 606/41 |
| 2018/0214202 A1 | 8/2018 | Howard et al. | |
| 2019/0030328 A1 | 1/2019 | Stewart et al. | |
| 2020/0205890 A1 | 7/2020 | Harlev et al. | |
| 2020/0229866 A1 | 7/2020 | Harlev et al. | |

OTHER PUBLICATIONS

European Patent Office Examination Report for Application No. 22715456.4 dated Feb. 12, 2025 (4 pages).

\* cited by examiner

PULSED FIELD ABLATION CATHETERS WITH ENHANCED FIELD SMART ELECTRODES

CROSS-REFERENCE TO RELATED APPLICATION

This application claims the benefit of U.S. Provisional Application Ser. No. 63/162,596 filed Mar. 18, 2021.

FIELD

The present technology is generally related to pulsed electric field (PEF) ablation and the use of passive electrodes to extend the electric field.

BACKGROUND

Pulsed electric field (PEF) ablation or pulsed field ablation (PFA) is an ablation modality in which high voltage pulses are delivered from one or more electrodes to cause electroporation of a target tissue. In a typical application, a catheter with a plurality of electrodes in communication with a PEF generator is advanced to a location proximate the tissue to be ablated. High voltage pulses are delivered in a bipolar or monopolar manner which causes the creation of an electric field which electroporates the target tissue.

PEF and PFA generally appear to be able to selectively target, for example, cardiomyocytes while sparring collateral tissue. This treatment modality appears to kill cells through mechanisms that do not alter stomal proteins, spare sensitive structures to improve safety, and do not sacrifice cardiomyocyte ablation efficiency. Many parameters can impact PEF or PFA outcomes including the pulse intensity, the waveform, shape, the number of pulses, and the electrode configuration and geometry.

The complexity of treatment using pulsed field ablation increases when the number of electrodes is increased and the reliability of the treatment can decrease with the increased number of electrodes. In certain treatments, it is desirable to enhance the field strength of the electrodes in certain directions. For example, it may be desirable to increase the electrode field strength in a forward direction. However, the size and shape of the created electric field is limited to the size and position of the electrodes with respect to the tissue. The physical and electrical characteristics must be carefully deployed to balance target tissue effects with collateral implications including temperature rise, muscle contraction, electrical arcing and other impacts. Increased sensitivity and specificity of sensing while maintaining a particular surface area during delivery is helpful to treat certain tissue within the body.

SUMMARY

The techniques of this disclosure generally relate to pulsed electric field ablation but include energies delivered for both therapeutic and diagnostic purposes, by effecting a desired level of hyperpermeablization in tissues. In one aspect, the present disclosure provides a medical device including an elongated body having a proximal portion and a distal portion. A plurality of active electrodes is coupled to the distal portion of the elongate body and are configured to electrically couple to a source of pulsed electric field energy. At least one passive electrode is coupled to the elongate body or is placed in another location in relation to the tissue targeted for ablation and is not configured to electrically couple to the source of pulsed electric field energy, the at least one passive electrode being configured to passively extend or focus an electric field generated by the plurality of active electrodes.

In one aspect of this embodiment, the at least one passive electrode is axially aligned with the plurality of active electrodes.

In one aspect of this embodiment, the at least one passive electrode is a guidewire slidably received within a portion of the elongate body and extending distally from the distal end of the elongate body.

In one aspect of this embodiment, the at least one passive electrode is a helical wire extending from a distal end of the distal portion of the elongate body.

In one aspect of this embodiment, the plurality of active portions is separated by an insulator disposed on the elongate body, and wherein the at least one passive electrode is disposed on the insulator.

In one aspect of this embodiment, the plurality of active electrodes is composed of tantalum, tantalum oxide, or a tantalum alloy.

In one aspect of this embodiment, the plurality of active electrodes includes at least a partial layer of tantalum oxide.

In one aspect of this embodiment, the plurality of active electrodes is disposed between a pair of the at least one passive electrodes.

In one aspect of this embodiment, the at least one passive electrode is composed of a conductive polymer.

In one aspect of this embodiment, the distal portion includes a balloon, and wherein the plurality of active electrodes and the at least one passive electrode are disposed on an outer surface of the balloon.

In one aspect, a medical system includes a generator configured to generate pulsed electric field (PEF) energy. A medical device is coupled to the generator, the medical device includes an elongate body having a proximal portion and a distal portion. A plurality of active electrodes is coupled to the distal portion of the elongate body and are configured to electrically couple to a source of pulsed electric field energy. At least one passive electrode is coupled to the shaft and not configured to electrically couple to the source of pulsed electric field energy, the at least one passive electrode being configured to passively extend or focus an electric field generated by the plurality of active electrodes.

In one aspect of this embodiment, the at least one passive electrode is axially aligned with the plurality of active electrodes.

In one aspect of this embodiment, the at least one passive electrode is placed on an independent catheter.

In one aspect of this embodiment, the at least one passive electrode is a guidewire slidably received within a portion of the elongate body and extending distally from the distal end of the elongate body.

In one aspect of this embodiment, the at least one passive electrode is a helical wire extending from a distal end of the distal portion of the elongate body.

In one aspect of this embodiment, each of the plurality of active portions is separated by an insulator disposed on the elongate body, and wherein the at least one passive electrode is disposed on the insulator.

In one aspect of this embodiment, the plurality of active electrodes is composed of tantalum, tantalum oxide, or a tantalum alloy.

In one aspect of this embodiment, the plurality of active electrodes includes at least a partial layer of tantalum oxide.

In one aspect of this embodiment, the at least one passive electrode is composed of a conductive polymer.

In one aspect of this embodiment, the plurality of active electrodes is disposed between a pair of the at least one passive electrodes.

In one aspect of this embodiment, the at least one passive electrode is placed on an independent catheter.

In one aspect, a medical device includes an elongate body having a proximal portion and a distal portion. A plurality of active electrodes is coupled to the distal portion of the elongate body and is configured to electrically couple to a source of pulsed electric field energy, the plurality of electrodes being composed of tantalum or a tantalum alloy. An insulator is disposed between adjacent ones of the plurality of active electrodes, the insulator being composed of tantalum pentoxide. A plurality of passive electrodes coupled to the elongate body and not configured to electrically couple to the source of pulsed electric field energy, the plurality of passive electrodes being configured to passively extend or focus an electric field generated by the plurality of active electrodes. One of the plurality of passive electrodes is disposed on an outer surface of the insulator.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 10 is side view of another embodiment of an exemplary distal portion of a medical device used with the

Figure 1:
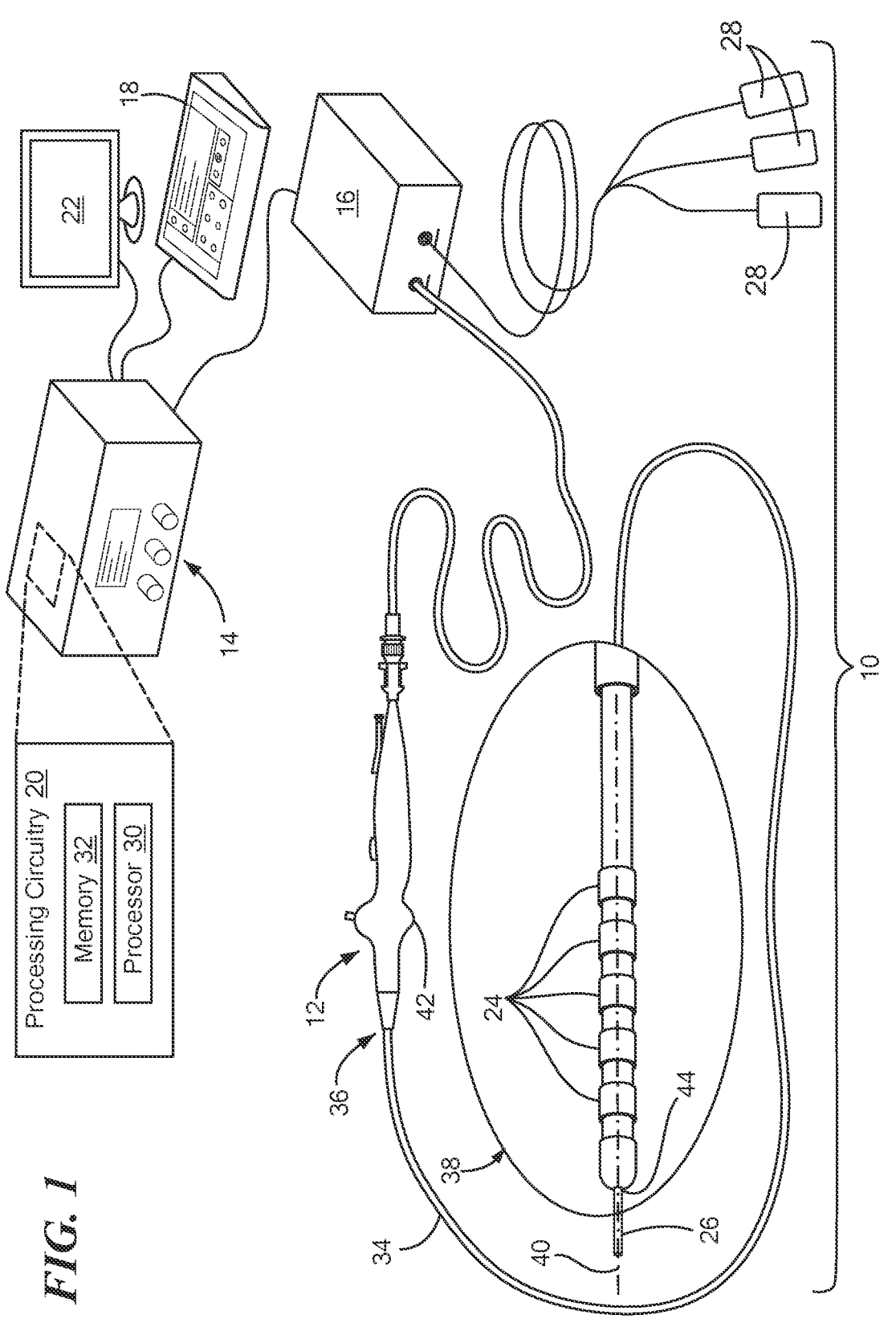
FIG. 1 is a system view of an exemplary pulsed electric field energy delivery system constructed in accordance with the principles of the present application.

4 system shown in FIG. 1 with passive electrodes disposed around a perimeter of active electrodes.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled directly to an energy supply, for example, a pulse field ablation generator 14 including an energy control, delivering, and monitoring system or indirectly through a catheter electrode distribution system ("catheter electrode system" or "CEDS") 16. The energy supply 14 may include an energy control, delivering and monitoring system. The energy supply 14 may be within or in electrical communication with a controller 18 having processing circuitry 20 that may further include or be in electrical communication with one or other system components such as one or more displays 22, the CEDS 16, the controller 18, active electrodes 24, passive electrodes 26, and the like. Such processing circuitry 20 may include functions to track the location in three-dimensional space of each electrode 24, 26 based on measurements of electrical potentials measured on each electrode 24, 26 or by the relative proximity to an electromagnetic element or elements which are tracked by a navigation system. For simplicity, all system components, other than the medical device may be collectively referred to as being part of the controller 18.

The controller 18 may be a remote controller in communication with the generator 14 for operating and controlling the various functions of the generator 14 and in further communication with a plurality of surface electrodes 28 configured to measure and record electrograms. The medical device 12 may generally include one or more diagnostic or treatment regions for energetic, therapeutic and/or investigatory interaction between the medical device 12 and a treatment site. The treatment region(s) may deliver, for example, pulsed electric field (PEF) energy sufficient to reversibly or irreversibly electroporate a tissue area, or radiofrequency energy in proximity to the treatment region (s). The controller 18 may be a remote controller that includes processing circuitry 20 configured to operate and control the various functions of the system 10. Alternatively, in some configurations the processing circuitry 20 may include a processor 30 and a memory 32. In particular, in addition to or instead of a processor, such as a central processing unit and memory, the processing circuitry 20 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 30 may be configured to access (e.g., write to and/or read from) the memory 32, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

The processing circuitry 20 may be configured to control any of the methods and/or processes described herein and/or to cause such methods, and/or processes to be performed, e.g., by the controller 18. Processor 30 corresponds to one or more processors 30 for performing functions described herein. The memory 32 is configured to store data, programmatic software code and/or other information described herein. In some embodiments, the software may include instructions that, when executed by the processor 30 and/or processing circuitry 20 causes the processor 30 and/or processing circuitry 20 to perform the processes described herein with respect to controller 18. For example, processing circuitry 20 of the controller 18 may be configured to perform one or more functions described herein such as with respect to methods and systems described in more detail herein.

The medical device 12 may include an elongate body or catheter 34 passable through a patient's vasculature and/or positionable proximate to a tissue region for diagnosis or treatment, such as a catheter, sheath, or intravascular introducer. The elongate body, shaft, or catheter 34 may define a proximal portion 36 and a distal portion 38 and may further include one or more lumens disposed within the elongate body 34 thereby providing mechanical, electrical, and/or fluid communication between the proximal portion 36 of the elongate body 34 and the distal portion 38 of the elongate body 34. The distal portion 38 may generally define the one or more treatment region(s) of the medical device 12 that are operable to monitor, diagnose, and/or treat a portion of a patient. The treatment region(s) may have a variety of configurations to facilitate such operation. In the case of purely bipolar pulsed field delivery, distal portion 38 includes electrodes that form the bipolar configuration for energy delivery. A plurality of active electrodes 24 may deliver in a bipolar fashion between selections of electrodes 24 or serve as one pole while a second device containing one or more electrodes (not pictured) would be placed to serve as the opposing pole of the bipolar configuration. Alternatively, the electrodes 24 may be arranged to deliver unipolar energy deliver between the plurality of electrodes 24 and the plurality of surface electrodes 28. As shown in FIG. 1, the medical device 12 may have a linear configuration with the plurality of active electrodes 24. For example, the distal portion 38 may include six active electrodes 24 linearly disposed along a common longitudinal axis 40. Alternatively, the distal portion 38 may include an electrode carrier arm or splines that is transitionable between a linear configuration and an expanded configuration in which the carrier arm or splines has an arcuate or substantially circular configuration. The carrier arm or splines may include the plurality of active electrodes 24 that are configured to deliver pulsed-field energy. Additionally, the carrier arm or splines may have at least one passive electrode 26. Further, the carrier arm when in the expanded configuration, may lie in a plane that is substantially orthogonal to the longitudinal axis of the elongate body 34. The planar orientation of the expanded carrier arm may facilitate ease of placement of the plurality of active electrodes 24 in contact with the target tissue. In yet another configuration, the distal portion may include a balloon with a plurality of electrodes 24 disposed on an outer surface of the balloon and configured to deliver pulsed-field energy.

Referring now to FIGS. 1-8, in some configurations, the at least one passive electrode 26 is coupled, directly or indirectly, or otherwise engaged to the elongate body 34. The at least one passive electrode 26 is a conductive element that is not coupled to a conductor that is coupled to a generator 14. That is, the at least one passive electrode 26 is not independently configured to delivery PEF energy. Rather, the at least one passive electrode 26 is configured to extend or focus PEF energy delivered by the plurality of active electrodes 24 to create particular ablation patterns. For example, according to aspects of this disclosure, at least one passive electrode 26 may be configured to focus the delivery of energy when the active electrodes 24 are delivering energy to tissue. When the electrode is an active electrode 24, current may be supplied to the electrode and when the electrode is a passive electrode 26 current may be carried away from the electrode to another grounded location. The energy that is delivered to the active electrode 24 may flow from the active electrode 24 through the tissue and then to the passive electrode 26 to provide a more focused area of energy delivery. For example, if passive electrodes 26 surround one active electrodes 24 when energy is being delivered to the active electrodes 24 the energy delivery pattern can be more focused in a specific location on particular tissue. Additionally, depending upon the placement of the active electrodes 24 and the passive electrodes 26, the energy delivery to the active electrodes 24 may be extended over a larger distance to a larger area of tissue to provide treatment to the tissue if there are a plurality of active electrodes 24 in a location such that the energy delivery may be more diffuse and extend to a greater area of tissue. For example, a plurality of active electrodes 24 may only have one or two passive electrodes 24 near the plurality of active electrodes 24 and this type of configuration may help to extend the delivery of energy to a larger more diffuse area of tissue. In some examples, using passive electrodes 26 may extend energy delivery to a focused area of tissue. Having the capability to organize/arrange passive and active electrodes 24, 26 in different configurations on the elongate body 34 may provide a cost effective way to target tissue treatment is particular manners using different organizations of passive electrodes 26 and active electrodes 24.

7

Figures 2, 3, 4:
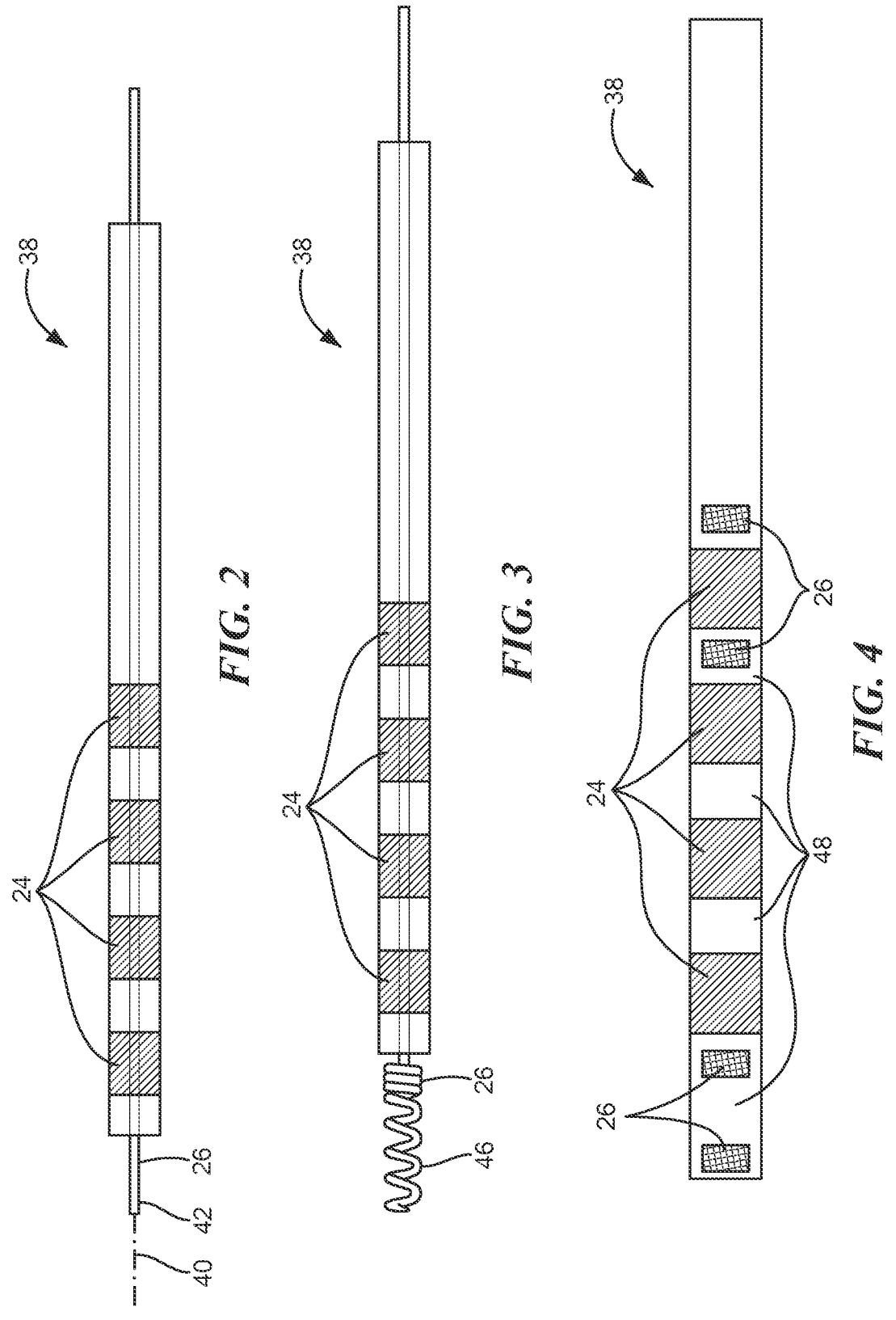
FIG. 2 is a side view of an exemplary distal portion of the medical device used with the system shown in FIG. 1.
FIG. 3 is side view of another embodiment of an exemplary distal portion of a medical device used with the system shown in FIG. 1.
FIG. 4 is side view of another embodiment of an exemplary distal portion of a medical device used with the system shown in FIG. 1 and showing an exemplary electric field generated by one or more passive electrodes.

The passive and active electrode configurations shown in a linear format in FIGS. 2-5 can also be used on the carrier arm or the splines. For example, as shown in FIG. 2, the at least one passive electrode 26 is a guidewire 42 slidably received within a portion of the elongated body 34 and extends distally from the distal end 44 of the elongate body 34. The distance that the guidewire 42 extends form the distal end 44 of the elongate body 34 changes the electric field. That is, the guidewire 42 extends the PEF generated by the plurality of active electrodes 24 by creating an electrical pathway between the active electrodes 24 and the guidewire 42. More specifically, the higher conductivity of the wire being the passive electrode 26 creates a locally preferential pathway for the electric field causing a focusing of the electric field around the passive electrode 26 in the presence of the PEF energy applied between the active electrodes 24. To convey more intuitively, because there is a more conductive path presented by the passive electrode 26, more field chooses to pass through that space which increases the field intensity around that element, thereby focusing the electric field in an area nearer to passive electrode 26 relative to the location of the passive electrodes 24. The active electrodes 24 and/or the passive electrodes 26 may be secured to the distal portion 38 and the distal portion 38 may be made from a non-conductive material including polyether block amide. The active electrodes 24 and/or the passive electrodes 26 may be glued, swaged, or otherwise secured to the distal portion 38. In the configuration shown in FIG. 2, the guidewire 42 is axially aligned with the active electrode 24 and extends along the common longitudinal axis 40. The guidewire 42 may extend out from the distal end 44 of the elongate body 34 depending upon the particular treatment being delivered as well as the size, type, and shape of the tissue being treated. In some embodiments, the guidewire 42 may be secured to the proximal portion 36 and the proximal portion 36 may include a handle or another type of gripping element. The guidewire 42 may be in the proximal portion 36 and the elongated body 34 and the guidewire 42 may extend through at least one or more lumens that are in communication with the distal portion 38 of the elongate body 34 to the distal portion 38 of the elongate body 34. The guidewire 42 may be within the lumen and in communication with the proximal portion 36 and the distal portion 38 such that the guidewire 42 may extend from the proximal portion 36 to the distal portion 38. Additionally, in some embodiments, the guidewire may extend from the distal end 44 of the elongate body 34. The guidewire 42 may also be movable in a variety of different directions when extending outwardly from the distal end 44 such as up, down, left and right. The proximal portion 36 including, for example, the handle or other gripping element, may be moved to allow for the advancement of the guidewire 42, the retraction of the guidewire 42 within the medical device 12, as well as to move the guidewire 42 in a variety of different directions. The proximal portion 36 may include various buttons and different movement mechanisms to allow for the movement of the guidewire 42 in different directions. Optionally, a portion of the guidewire 42 may be a conductive meaning that a portion of the guidewire 42 can conduct energy and sliders, levers, dials, or other mechanisms may be part of the proximal portion 36 such as the handle to allow for to control various portions of the medical device 12 including the guidewire 42.

At least a portion of the guidewire 42 may also be composed of non-conductive material and a secondary tool/ medical treatment device may also be integrated with or used with the guidewire 42 as well. Additionally, the guidewire 42 may have at least one active electrode 24 and when the guidewire 42 can conduct energy the guidewire 42 may be in communication with the CEDS 16 or another energy supply to delivery energy to the active electrode 24 or other conductive portion that is part of the guidewire 42.

Referring now to FIG. 3, in another configuration, the at least one passive electrode 26 is a helical conductor 46, such as a wire, extending from the distal end of the elongate body 34. The helical conductor 46 can be tightly wound or more loosely wound as shown in FIG. 3 and the number of different windings as well as how tightly or loosely wound the helical conductor 46 may depend upon where treatment is being delivered as well as the type of tissue that is being treated. In one configuration, the helical conductor 46 is fixed at the distal end 44 of the elongate body 34 and extends outwardly from the distal end 44. The helical conductor 46 may be more tightly wound where it is fixed at the distal end of the elongate body and the windings of the helical structure may widen as the helical conductor 46 extends outwardly from the tip and the tip may have an anchoring portion. This shape allows the helical conductor 46 to be inserted into tissue and the tip may be anchored within the tissue so that the distal portion 38 may be used to deliver treatment to a particular tissue. The helical conductor 46 can be a variety of different shapes and sizes depending upon the particular treatment being delivered as well as the size, type and shape of the tissue being treated. The helical conductor 46 may also be movable in a variety of different directions when extending outwardly from the distal end 44 such as up, down, left, and right. In other configurations, the helical conductor 46 is slidably disposed within a portion of the elongate body 34 and can be advanced and retracted from the distal end 44 of the elongate body 34. The helical shape of the helical conductor 46 allows potential active fixation to the target tissue in addition to a focusing of the applied PEF energy. Where an exemplary helical conductor 46 is more loosely wound and has the same protrusion distance, radius, and gauge as a more tightly wound helical conductor 46, the more tightly wound helical conductor 46 may offer a larger surface area of the helical conductor 46 in a similar volume which can change the current density at the surface. Additionally, adjusting how tightly or loosely wound the helical conductor 46 is can also allow for different treatments involving different tissues. It will also be understood that the helical conductor 46 may also be transitioned from a passive electrode 26 into an active electrode 24 depending on the type of treatment being delivered to tissue. Having the helical conductor 46 as an active electrode 24 or a passive electrode 26 may focus the energy delivery on particular tissue or extend the energy delivery pattern to a larger area of tissue depending upon whether the helical conductor 46 is an active electrode 24 or a passive electrode 26. For example, if the helical conductor 46 is a passive electrode 26 and at least one active electrode 24 disposed near the helical conductor 46, the delivery of energy may be more focused on particular tissue rather than providing a more extended and diffuse energy delivery. Alternatively, if the helical conductor 46 is an active electrode 24 and is surrounded by further active electrodes 24 the energy delivery may be more extended and diffuse thereby impacting a greater amount of tissue.

Referring now to FIG. 4, disposed between the active electrodes 24 may be insulator 48 disposed about a portion of the elongate body 34. The insulator 48 may be, for example, tantalum pentoxide or other insulating materials that prevent delivery of low voltage pulses but allows high voltage pulses or a polymeric material. The at least one passive electrode 26, which may be a ring electrode or a conductive coating, for example, a coating of tantalum, tantalum oxide, or a conductive polymer, may be disposed on an outer surface of the insulator 48 to create particular ablation patterns. The size and shape of the insulator 48 can create different ablation patterns depending upon the type of treatment that is being delivered to the tissue.

In the configuration shown in FIG. 4, a pair of the least one passive electrode 26 is disposed distal to the most distal active electrode 24 and a pair of the at least one passive electrode 26 is disposed on opposite sides of the most proximal active electrode 24. The orientation of the electric field will depend upon where the insulator 48 is disposed as well as where the passive electrodes 26 and active electrodes 24 are placed along the elongate body 34. Furthermore, the orientation of the electric field may be different depending upon the size and of the active and passive electrodes 24, 26 as well as the size of any insulator 48. The delivery of the electric field can be customized to the patient and the type of treatment being delivered to the tissue. The insulator 48 can help to amplify the treatment field that be being delivered to the tissue. Depending upon the placement of the insulator 48 relative to the active and passive electrodes 24, 26 can focus or extend the electric field when energy is delivered to the active electrodes 24. For example, if the active electrodes 24 are surrounded by insulators 48, the delivery of energy may be more focused on a discrete area of tissue as the insulators 48 may inhibit how diffusely energy is delivered. Alternatively, if the active electrodes 24 are not surrounded by insulators 48, the delivery of energy may be extended to a larger area of tissue as the delivery of energy is not inhibited.

Figures 5, 6:
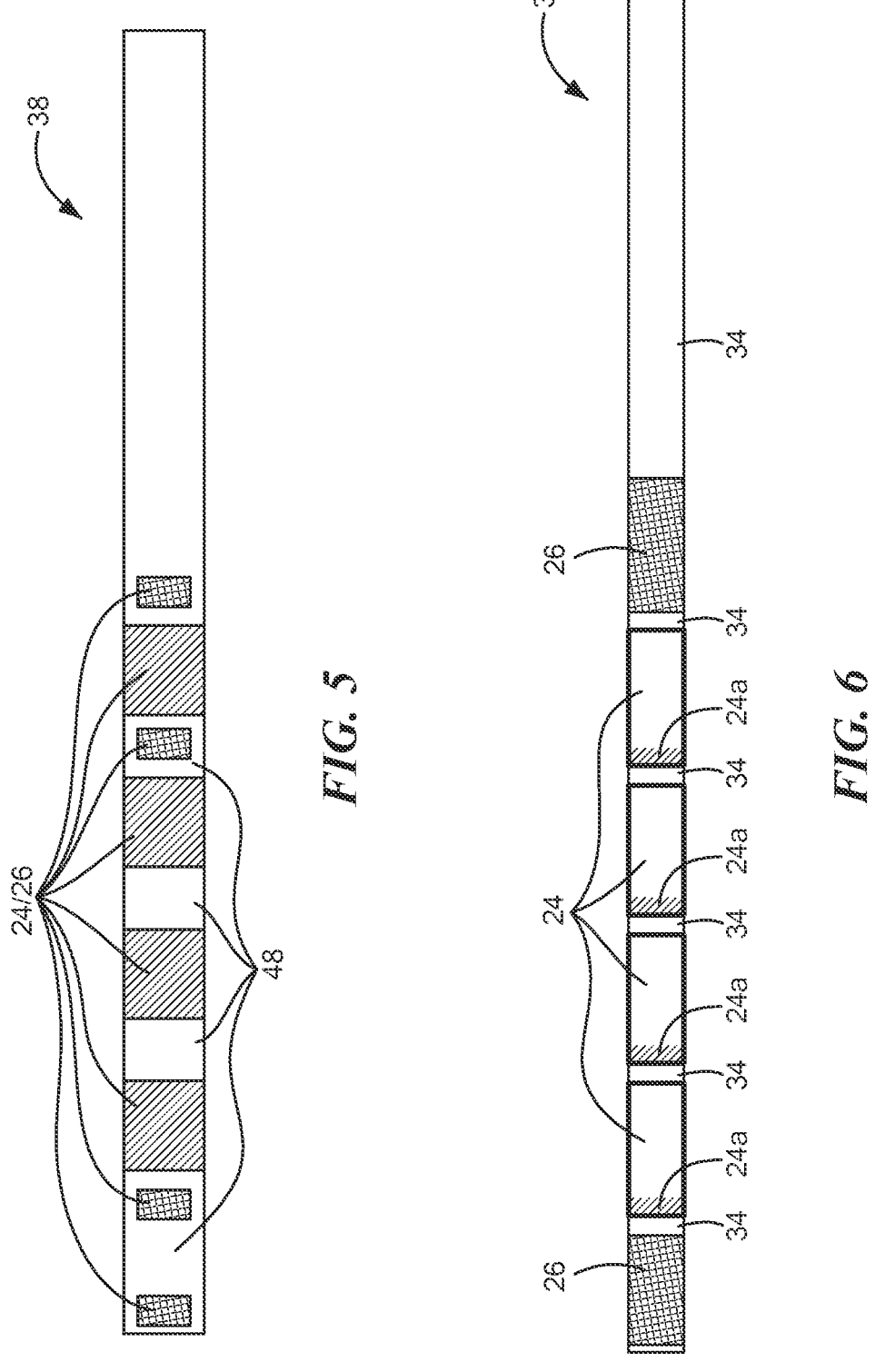
FIG. 5 is side view of another embodiment of an exemplary distal portion of a medical device used with the system shown in FIG. 1.
FIG. 6 is side view of another embodiment of an exemplary distal portion of a medical device used with the system shown in FIG. 1.

Referring now to FIG. 5, in another configuration, the active electrodes 24 and the passive electrodes 26 may be interchangeable. The active electrodes 24 and passive electrodes 26 can be disposed on a portion of the elongate body 34 in varying combinations and in different locations. The insulator 48 may also be disposed about a portion of the elongate body 34. The positions of the active electrodes 24, the passive electrodes 26, and insulator 48 can be depending upon the what type of electric field would be preferable for a particular treatment being delivered to the tissue. Further, the active electrodes 24 and the passive electrodes 26 are both independently configured to be switched on and off to further customize the electric field and the treatment of the tissue. For example, if more targeted treatment is desired for particular treatment, an active electrode 24 may be surrounded by passive electrodes 26 and/or insulators 48 to focus the delivery of energy to a particular area of tissue. Alternatively, the elongate body 34 may have a plurality of active electrodes 24 near one another without passive electrodes 26 and/or insulators 48 and this can extend the delivery of energy to a larger area of tissue.

Referring now to FIG. 6, in another configuration, the active electrodes 24 are composed of tantalum or a tantalum alloy and are substantially coated, anodized, or otherwise layered with tantalum oxide, i.e., pentoxide as labeled by "24a". For example, in one configuration, about 90% of the surface of the active electrodes 24 are anodized or layered with tantalum oxide to reduce far-field electrograms. Alternatively, in another configuration only about 10-15% of the surface of the active electrodes 24 are anodized or layered with tantalum oxide to reduce far-field electrograms. Having the active electrodes 24 at least partially composed of tantalum or a tantalum alloy and are substantially coated, anodized, or otherwise layered with tantalum oxide, i.e., pentoxide can prevent or minimize low frequency or direct current voltage collection as the oxide generally allows the passing of mostly high frequency current. Having the active electrodes 24 at least partially composed tantalum or a tantalum alloy and are substantially coated, anodized, or otherwise layered with tantalum oxide can help focus the delivery of high frequency current to the tissue. Additionally, in another configuration, each electrode may have at least two sides and about 10% of each side of each active electrode 24 may not be oxidized and would therefore be exposed. The other 90% of each side of the active electrode 24 would be oxidized in the center of each side. Having this type of configuration may result in improved far field signal rejection while still allowing a large surface area for the delivery of energy. In such a configuration, the exposed non-anodized regions of the active electrodes 24 may be used for sensing and mapping and the anodized portion will be included for delivery of PEF energy. In this particular configuration, the non-anodized portion of the active electrode 24 is disposed at the distal end of each electrode 24 such that a non-anodized portion of one of the active electrodes 24 is adjacent an anodized portion of an adjacent electrode 24. In the configuration shown in FIG. 6, the active electrodes 24 are disposed between a pair of the at least one passive electrode 26. Also, each active electrode 24 may be spaced apart on the elongate body 34 such that as shown in FIG. 6 each active electrode 24 is spaced apart from one another and is separated by a portion of the elongate body 34. The oxide that is present in each active electrode 24 may limit the low frequency transmission of energy, but high frequency energy delivery may pass freely between the active electrodes 24 during the delivery of energy to the active electrodes 24. The active electrodes 24 may be spaced apart by equal sized portions of the elongate body 34 or they may be spaced apart by different sized portions of the elongate body 34. As shown in FIG. 6, the active electrodes 24 are spaced apart by equal sized portions of the elongate body 34 and the passive electrodes 26 are spaced apart from the active electrodes 24 with an equal sized portion of the elongate body 34. The passive electrodes 26 may alternatively be unpowered electrodes which are positioned between or near powered or active electrodes 24. For example, if every other electrode in a series of electrodes is energized such that every other electrode is an active electrode 24 that is energized and the electrodes between the active and energized electrodes 24 are passive and not energized, this may allow for the passive extension of the electric field distribution. This type of energizing pattern may be used to limit excessive currently flow from closely spaced active electrodes 24 if all the active electrodes 24 were to be energized at opposite polarities with such close spacing and large overall electrode surface areas. Accordingly, during the delivery of energy to the electrodes 24, 26, some energy delivery may be done by leaving particular active electrodes 24 unpowered such that some of the active electrodes 24 become passive. This energy delivery may be followed by one or more alternate sets of electrodes 24/26 receiving energy delivery while others do not receive the energy delivery. Having this type of energy delivery to the active and passive electrodes 24 and 26 can allow a more uniform and more well distributed range of tissue exposure to the high electric field gradients.

Figures 7, 8:
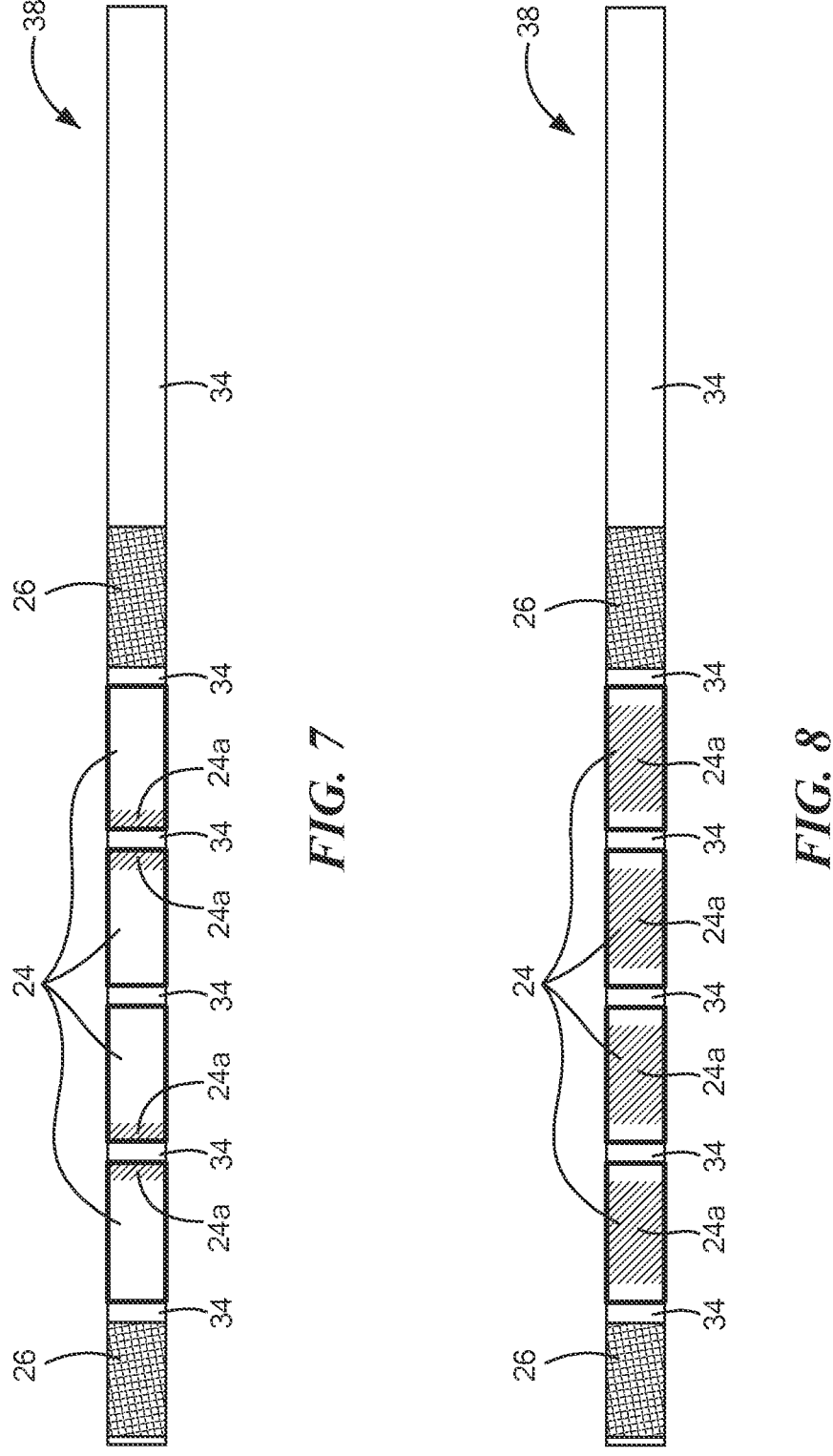
FIG. 7 is side view of another embodiment of an exemplary distal portion of a medical device used with the system shown in FIG. 1.
FIG. 8 is side view of another embodiment of an exemplary distal portion of a medical device used with the system shown in FIG. 1.

In the configuration shown in FIG. 7, the exposed portions of adjacent electrodes 24 are positioned adjacent to each other for bipolar sensing. This allows for a more localized measurement of EGM activity for example when targeting cardiomyocytes. The active electrodes 24 are shown disposed between the pair of the at least one passive electrode 26. The non-anodized portion of the active electrode 24 is on alternating distal end and proximal end of each active electrode 24 so that each non-anodized portion of each active electrode 24 is positioned next to another non-anodized portion of each active electrode 24 and each active electrode 24 is separated by a portion of the elongate body 34. In the two active electrodes 24 that are in the two center electrodes 24 in FIG. 7, the anodized portion of the active electrodes 24 are positioned next to each other as well. As shown in FIG. 7, each portion of the elongate body 34 is the same size such that the spacing between each active electrode 24 is the same. However, the size of each portion of the elongate body 34 that is separating the active electrodes 24 may be differently sized depending upon the type of treatment being delivered as well as the type of tissue that that the treatment is being used on.

In the configuration shown in FIG. 8, the active electrodes 24 are about 90% exposed and only about 10% coated with tantalum oxide. Alternatively, the active electrodes 24 may have 25% coated with tantalum oxide and 75% exposed. Such configurations reduce edge effects, i.e., overheating at the edges of the electrodes owing to increased current. Also, these configurations may help to reduce current concentrations at electrode edges that may result in, for example, bubble formation. The reduction of far-field signals may also be experienced using this configuration by reducing the amount of the electrode that is able to pass low frequency signals. The active electrodes 24 are shown disposed between the pair of the at least one passive electrode 26. As shown in the active electrodes 24 in FIG. 8, the distal end and the proximal end of each active electrode 24 is coated with tantalum oxide while the center portion of each electrode is exposed. The distal end and proximal end of each active electrode 24 that is coated with tantalum oxide is proximate another distal end or proximal end of one of the other active electrodes 24. Additionally, each active electrode is spaced apart by a portion of the elongate body 34. The center portion of each active electrode 24 is exposed electrode and is not coated with tantalum oxide.

Figure 9:
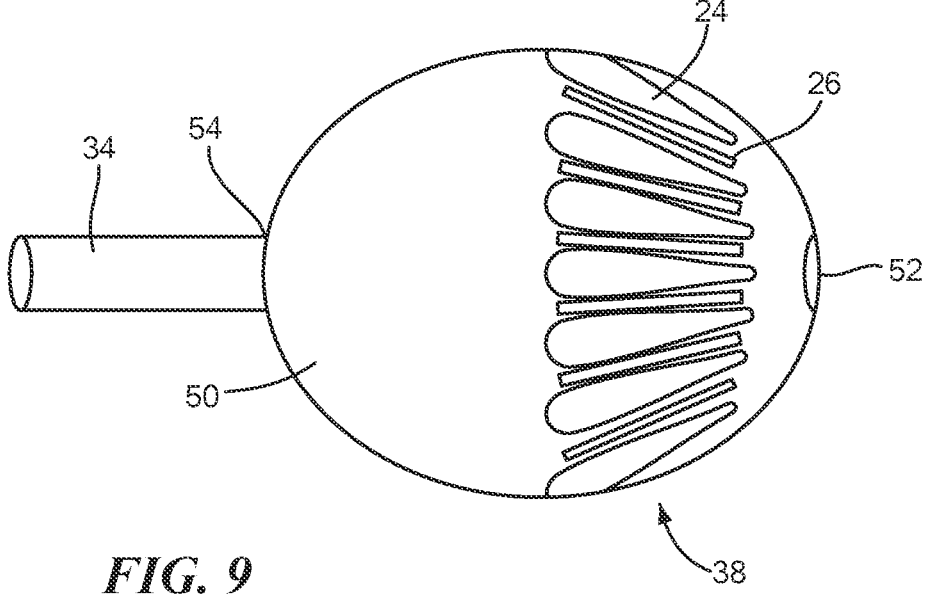
FIG. 9 is side view of another embodiment of an exemplary distal portion of a medical device used with the system shown in FIG. 1 with passive electrodes disposed between active electrodes.
Figure 10:
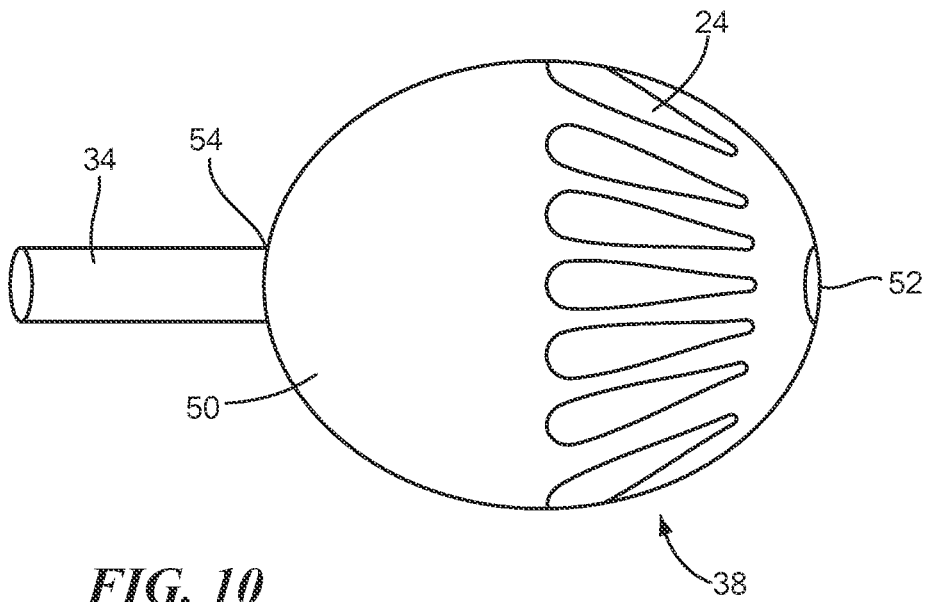

Referring now to FIGS. 9 and 10, disposed at the distal end 44 of the elongate body 34 may be an expandable member 50, for example, a balloon. Disposed on the outer surface of the balloon 50 may the active electrodes 24 in any number and in any shape or size. For example, as shown in FIG. 9, the active electrodes 24 define substantially teardrop shapes. The active electrodes 24 may be disposed around the entire circumference of the expandable member 50 or only a portion of the expandable member 50. As shown in FIG. 9, there are seven active electrodes 24 visible, but it will be understood that there may be more or less active electrodes 24 on the expandable element 50. The size, shape and orientation of the active electrodes 24 may depend upon what type of treatment is being delivered, where the treatment is being delivered, as well as the size of area where the treatment is being delivered. The expandable member 50 may have a distal end 52 and a proximal end 54 opposite the distal end 52. The proximal end 54 may be secured to the elongate body 34 and the elongate body 34 may run through the expandable member 50 from the proximal end 54 to the distal end 52 or the elongate body 34 distal end 44 may be secured to the proximal end 54 of the expandable member 50. In one configuration, as shown in FIG. 9, the at least one passive electrode 26 is disposed between two adjacent active electrodes 24 or near an active electrode 24. As shown in FIG. 9, there are six visible passive electrodes 26, but it will be understood that there can be more or less passive electrodes 26 on the expandable element 50. The passive electrodes 26 may be on the entire circumference of the expandable member 50.

Now referring to FIG. 10, there are active electrodes 24 on the expandable element 50. In FIG. 10 there are seven visible active electrodes 24, but there may be more of less active electrodes 24 on the expandable element 50. In the configuration as shown, the perimeter of each active electrode 24 may be anodized in whole or in part with tantalum oxide to reduce edge effect. Having the perimeter anodized can reduce conductivity. For example, the entire perimeter of each active electrode 24 may be anodized or only a portion of the perimeter of each active electrode 24 may be anodized. Alternatively, certain active electrodes 24 may have the entirety of their perimeter or only a portion of their perimeter anodized while other active electrodes 24 may not have any anodization. Having these different types and patterns of anodization allows for different treatment patterns. Additionally, in the configuration as shown in FIG. 9, every other active electrode 24 in the series may be energized such that every other electrode is an energized active electrode 24 and the electrodes between the active and energized electrodes 24 are passive electrodes 24 that are not energized. This type of energy delivery pattern allows the passive extension of the electric field distribution and may also be used to limit excessive current flow from closely spaced active electrodes 24 if all the active electrodes 24 were to be energized at opposite polarities with such close spacing and large overall electrode surface areas. During the delivery of energy to the active electrodes 24, some energy delivery may be done by leaving particular active electrodes 24 unpowered such that the active electrodes 24 become passive. This energy delivery may be followed by one or more alternate sets of active electrodes 24 receiving energy delivery while others do not receive energy delivery. Having this type of energy delivery can allow a more uniform and more well distributed range of tissue exposure to the high electric field gradients.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongated body having a proximal portion and a distal portion;
   a plurality of active electrodes coupled to the distal portion of the elongate body and being configured to electrically couple to a source of pulsed electric field energy and receive a pulse train including low voltage pulses and high voltage pulses;
   an insulator disposed between adjacent ones of the plurality of active electrodes, the insulator being composed of tantalum pentoxide and being configured to prevent delivery of the low voltage pulses and allow delivery of the high voltage pulses; and
   at least one passive electrode coupled to the elongate body and disposed on the insulator, the at least one passive electrode to the source of pulsed electric field energy during delivery of the pulse train, the at least one passive electrode composed of a conductive material and configured to passively extend or focus an electric field generated by the plurality of active electrodes.

2. The device of claim 1, wherein the at least one passive electrode is axially aligned with the plurality of active electrodes.

3. The device of claim 1, wherein each of the plurality of active electrodes is separated by the insulator disposed on the elongate body.

4. The device of claim 1, wherein at least one of the plurality of active electrodes is composed of tantalum or a tantalum alloy.

5. The device of claim 4, wherein the plurality of active electrodes includes at least a portion of a surface having a layer of oxide.

6. The device of claim 1, wherein the at least one passive electrode is composed of tantalum or a conductive polymer.

7. A medical system, comprising:
  a generator configured to generate pulsed electric field (PEF) energy; and
  a medical device coupled to the generator, the medical device including:
    an elongate body having a proximal portion and a distal portion;
    a plurality of active electrodes coupled to the distal portion of the elongate body and being configured to electrically couple to the generator and receive a pulse train of PEF energy include low voltage pulses and high voltage pulses;
    an insulator disposed between adjacent ones of the plurality of active electrodes, the insulator being composed of tantalum pentoxide and being configured to prevent delivery of the low voltage pulses and allow delivery of the high voltage pulses; and
    at least one passive electrode coupled to the elongate body and disposed on the insulator, the at least one passive electrode is not electrically coupled to the generator during delivery of the pulse train, the at least one passive electrode composed of a conductive material and configured to passively extend or focus an electric field generated by the plurality of active electrodes.

8. The system of claim 7, wherein the at least one passive electrode is axially aligned with the plurality of active electrodes.

9. The system of claim 7, wherein each of the plurality of active electrodes is separated by the insulator disposed on the elongate body.

10. The system of claim 7, wherein the plurality of active electrodes is composed of tantalum or a tantalum alloy.

11. The system of claim 10, wherein the plurality of active electrodes includes at least a partial layer of oxide.

12. The system of claim 7, wherein the at least one passive electrode is composed of tantalum or a conductive polymer.

13. A medical device, comprising:
  an elongate body having a proximal portion and a distal portion;
  a plurality of active electrodes coupled to the distal portion of the elongate body and being configured to electrically couple to a source of pulsed electric field energy and receive a pulse train including low voltage pulses and high voltage pulses, the plurality of active electrodes being composed of tantalum or a tantalum alloy;
  an insulator disposed between adjacent ones of the plurality of active electrodes, the insulator being composed of tantalum pentoxide and being configured to prevent delivery of the low voltage pulses and allow delivery of the high voltage pulses;
  a plurality of passive electrodes coupled to the elongate body and is not electrically coupled to the source of pulsed electric field energy during delivery of the pulse train, the plurality of passive electrodes is composed of a conductive material and configured to passively extend or focus an electric field generated by the plurality of active electrodes; and
  one of the plurality of passive electrodes being disposed on an outer surface of the insulator.

* * * * *